United States Patent
Sigg et al.

(10) Patent No.: US 8,126,549 B2
(45) Date of Patent: Feb. 28, 2012

(54) CARDIAC PROTECTION SYSTEM AND METHOD

(75) Inventors: Daniel C. Sigg, St. Paul, MN (US);
James A. Coles, Jr., Minneapolis, MN (US); Dwight H. Warkentin, Arden Hills, MN (US); Deborah Ann Jaye, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 724 days.

(21) Appl. No.: 12/173,780

(22) Filed: Jul. 15, 2008

(65) Prior Publication Data
US 2010/0016740 A1 Jan. 21, 2010

(51) Int. Cl.
*A61N 1/362* (2006.01)
(52) U.S. Cl. .......................................... 607/9
(58) Field of Classification Search .................. None
See application file for complete search history.

(56) References Cited

U.S. PATENT DOCUMENTS

| | | | |
|---|---|---|---|
| 6,973,349 B2 | 12/2005 | Salo | |
| 7,103,410 B2 | 9/2006 | Kramer et al. | |
| 7,215,997 B2 | 5/2007 | Yu et al. | |
| 7,295,874 B2 | 11/2007 | Prinzen et al. | |
| 7,567,836 B2 * | 7/2009 | Zhang | 600/512 |
| 7,668,594 B2 * | 2/2010 | Brockway et al. | 607/9 |
| 2005/0075673 A1 | 4/2005 | Warkentin et al. | |
| 2006/0149326 A1 | 7/2006 | Prinzen et al. | |
| 2006/0241704 A1 | 10/2006 | Shuras et al. | |
| 2006/0259087 A1 * | 11/2006 | Baynham et al. | 607/9 |
| 2006/0287684 A1 * | 12/2006 | Baynham et al. | 607/9 |
| 2007/0150005 A1 | 6/2007 | Sih et al. | |
| 2007/0203524 A1 | 8/2007 | Sheldon et al. | |
| 2008/0004669 A1 | 1/2008 | Sathaye et al. | |

OTHER PUBLICATIONS

Vanagt et al. "Pacing-Induced Dys-Synchrony Preconditions Rabbit Myocardium Against Ischemia/Reperfusion Injury". Circulation: Journal of the American Heart Association, DOI: 10.1161, pp. I-264 to I-269, Jul. 5, 2006.
International Search Report, PCT/US2009/048602, 3 pages.

* cited by examiner

*Primary Examiner* — Kennedy Schaetzle
(74) *Attorney, Agent, or Firm* — Stephen W. Bauer; Michael J. Ostrom

(57) ABSTRACT

A cardiac ischemic protection system and method for conditioning a patient's heart is provided. The method can include detecting acute myocardial infarction, angina pectoris, silent ischemia, or stunning and providing closed-loop dyssynchronous pacing to the patient's heart to precondition and/or postcondition the patient's heart in order to reduce ischemic damage.

21 Claims, 3 Drawing Sheets

CARDIAC PROTECTION SYSTEM AND METHOD

TECHNICAL FIELD

This disclosure relates generally to cardiac conditioning systems and methods and more particularly to a cardiac ischemic protection system.

BACKGROUND

Very commonly, there is a significant delay between the onset of myocardial infarction and treatment. After acute myocardial thrombosis (i.e., acute myocardial infarction), the myocardial tissue initially becomes ischemic (i.e., a mismatch between oxygen supply and oxygen demand) and subsequently becomes necrotic (i.e., cell death). As myocardial tissue undergoes necrosis after approximately 20 to 30 minutes, early treatment and early revascularization is critical in order to salvage myocardium and prevent progressive cell death.

SUMMARY

In one or more embodiments, a method of providing cardiac ischemic protection to a patient's heart is provided. The method can include detecting acute myocardial infarction, angina pectoris, silent ischemia, or stunning. The method can include providing closed-loop dyssynchronous pacing to the patient's heart to precondition and/or postcondition the patient's heart in order to reduce ischemic damage.

In one or more embodiments, a cardiac ischemic protection system that conditions a patient's heart is provided. The system includes a detector that detects acute myocardial infarction, angina pectoris, silent ischemia, or stunning. The system also includes a pulse generator that provides closed-loop dyssynchronous pacing to the patient's heart to precondition and/or postcondition the patient's heart in order to reduce ischemic damage.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
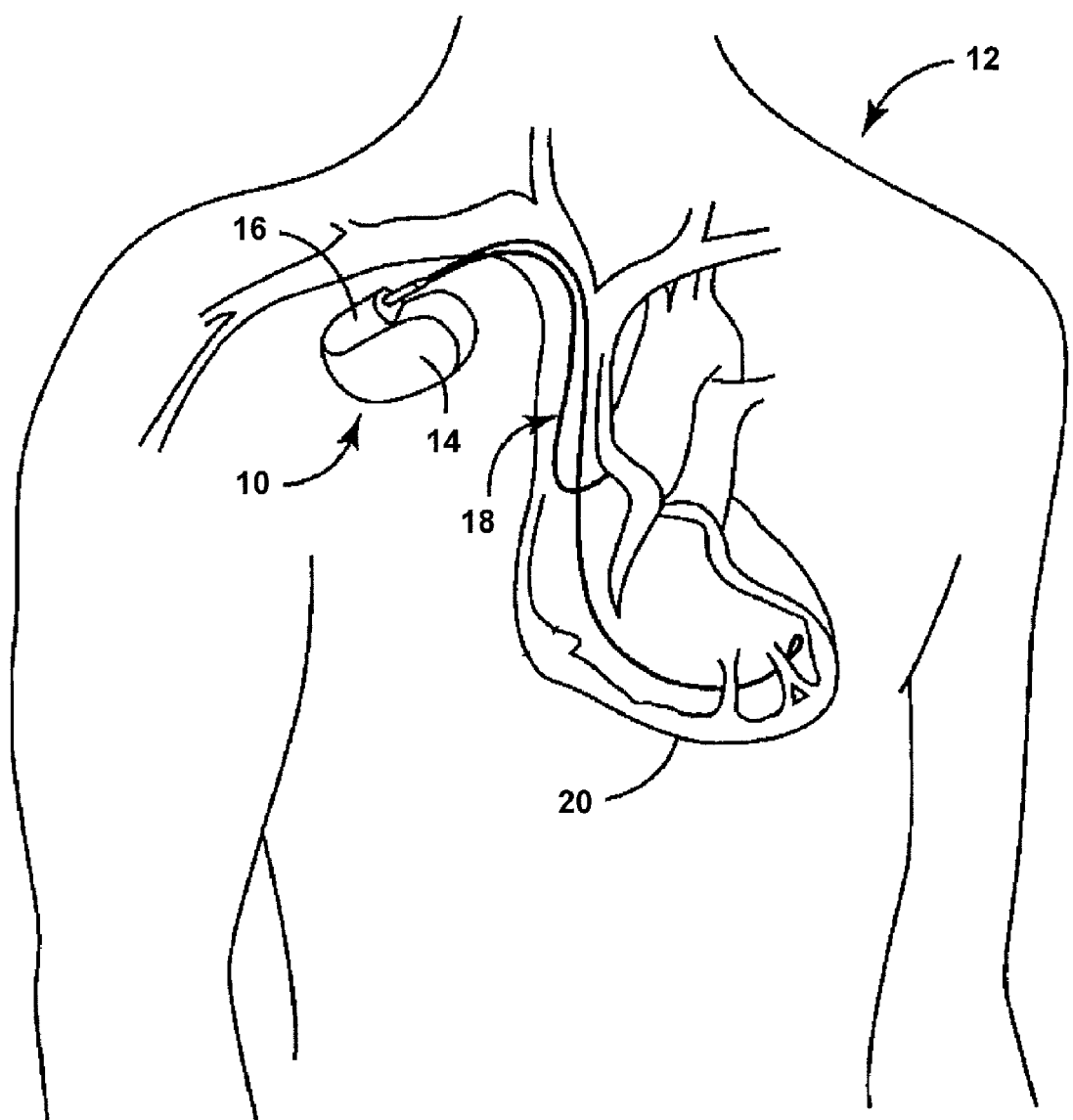
FIG. 1 is a schematic diagram of an implantable pacing device in accordance with an embodiment of the present disclosure.

The present disclosure describes a system including a detector that triggers deliberate asynchronous or dyssynchronous pacing to induce cardiac ischemic protection. The terms "asynchronous pacing" and "dyssynchronous pacing" both generally refer to cardiac pacing which produces inharmonious electrical and/or mechanical activation of the ventricles. More specifically, this type of cardiac pacing results in discordant motion of the ventricular walls which alters ventricular wall stresses and consequently myocardial perfusion. The wall motion discordance could be within a single ventricle (intra-ventricular) or between ventricles (inter-ventricular) or could be both intra and inter-ventricular. Initiating electrical activation from sites in the heart that are not associated with the His-Purkinje conduction system (for instance, the right ventricular apex) can achieve asynchronous or dyssynchronous pacing. Asynchronous or dyssynchronous pacing may induce cardiac ischemic protection effects similar to ischemic preconditioning and postconditioning.

The deliberate asynchronous or dyssynchronous pacing according to the present disclosure can occur immediately after onset of a sensed acute myocardial infarction, unstable angina pectoris, or other ischemic syndromes (i.e., silent ischemia, stunning, and hibernation) and can be started in a closed-loop fashion. Stunning can be defined as prolonged dysfunction following longer ischemic insults and is associated with decreased myocardial function following ischemia with normal or near-normal blood flow. Some embodiments of the invention can be used to help prevent stunning.

Once the device senses an ischemic syndrome, an asynchronous or dyssynchronous pacing algorithm can be automatically initiated through the device. A programmable threshold of ischemic burden can be used to trigger activation of the pacing algorithm (i.e., to automatically initiate and perform the pacing algorithm in a closed-loop fashion). Alternatively, an asynchronous or dyssynchronous pacing algorithm can be manually initiated by the patient or a bystander at the onset of symptoms related to an acute myocardial infarction. An external wireless patient activator can send a signal to the implantable device upon manual activation.

Upon activation of the algorithm (whether automatic or manual), an alert feature can simultaneously alert the patient and/or the medical personnel to help ensure the appropriate treatment, such as revascularization. The asynchronous or dyssynchronous pacing can delay the progression of cell death and provide additional time in which the myocardium can be salvaged. This may not only prevent future progression to heart failure, but may also prevent acute complications, such as extensive infarctions with acute heart failure, acute ventricular aneurysms and cardiac rupture, acute cardiac death, and acute arrhythmias.

In the following description, embodiments are set forth in order to provide a thorough understanding of the invention. It will be apparent, however, to one skilled in the art, that these and other embodiments may be practiced without these specific details. In some instances, features well-known to those skilled in the art have not been described in detail in order not to obscure the present disclosure.

FIG. 1 is a simplified schematic view of an implantable pacing device 10 that is implanted in a human body 12. The implantable pacing device 10 can include a hermetically-sealed enclosure 14 and connector module 16 for coupling the implanted pacing device 10 to electrical leads 18 arranged within the body 12, such as pacing and sensing leads 18 connected to portions of the heart 20 for delivery of pacing pulses to a patient's heart 20 and sensing of the heart 20 conditions. While the implantable pacing device 10 is depicted in a pacemaker configuration in FIG. 1, the implantable pacing device 10 can comprise any suitable type of implantable pacing device including, but not limited to, an implantable pulse generator, an implantable cardioverter-defibrillator or an implantable combination pacemaker-cardioverter-defibrillator.

Figure 2:
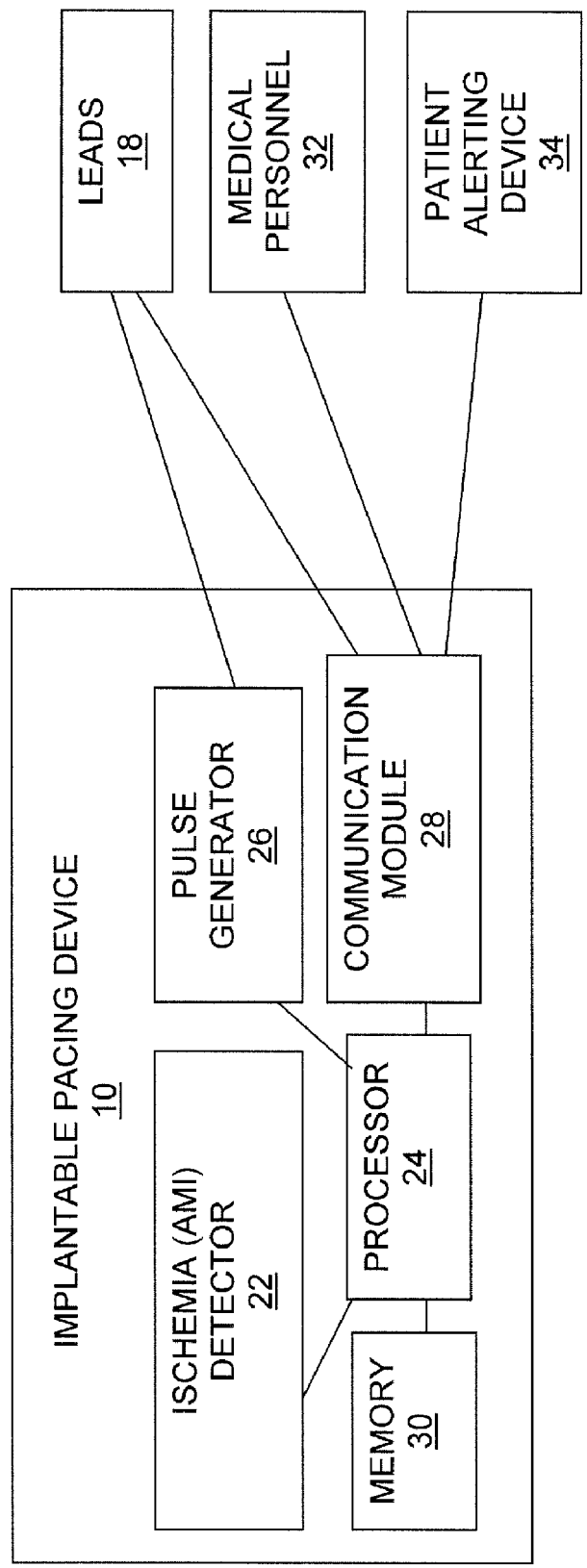
FIG. 2 is a block diagram illustrating a cardiac ischemic protection system including an implantable pacing device in accordance with an embodiment of the present disclosure.

FIG. 2 illustrates a simplified block diagram of a cardiac ischemic protection system including the implantable pacing device 10. In some embodiments, the implantable pacing device 10 can include a detector 22 (such as an acute myocardial infarction detector), a processor 24, a pulse generator 26, a communication module 28, and memory 30. The pulse generator 26 can provide pulses to the leads 18. The implantable pacing device 10 can communicate with medical personnel 32 and/or a patient alerting device 34.

The detector 22 can detect an acute myocardial infarction or other ischemic syndromes and can communicate with the processor 24, which can control the pulse generator 26. The processor 24 and the pulse generator 26 can provide asynchronous or dyssynchronous pacing in order to induce cardiac ischemic protection. In some embodiments, the detector 22 can detect ST segment changes and can initiate periodic pacing to "precondition" and/or "postcondition" the heart. In one embodiment, a precondition protocol can include three periods of about five minutes of pacing with intermittent periods of intrinsic (i.e., not paced, supraventricular, preferably sinus) rhythm of about five-minutes. In one embodiment, a precondition protocol can include continuous pacing. The postconditioning protocol can occur after the onset of an index ischemia or prolonged ischemia.

Simultaneously with the asynchronous or dyssynchronous pacing, the patient can be alerted through the patient alerting device 34 and can be instructed to seek treatment. The treatment after the postconditioning asynchronous or dyssynchronous pacing protocol can include one or more of the following: reperfusion therapy, revascularization, percutaneous transluminal coronary angioplasty, stent therapy, thrombolysis, coronary artery bypass graft, and heparinization and other drug therapies (such as beta-blockers, aspirin, cellular therapies, etc.). The patient's heart 20 can be protected by the postconditioning asynchronous or dyssynchronous pacing protocol until the patient can receive treatment.

In one embodiment, if the implantable pacing device 10 is a single chamber ventricular pacemaker (VVI) with a lead in the right ventricular apex, the pulse generator 26 can pace at a rate of about five beats greater than the sinus or intrinsic rate to delay or protect the myocardium from cell death.

In one embodiment, if the implantable pacing device 10 is a dual chamber ventricular pacemaker with leads in the right atrial appendage and the right ventricular apex, the pulse generator 26 can pace a lead (e.g., VDD-40) in the right ventricular apex with a short-sensed atrioventricular delay (e.g., about 30 milliseconds). The heart rate can be driven by the sinus rate so that oxygen demand does not substantially increase. During myocardial ischemia, where there is already an imbalance between oxygen supply and demand, one does not need to substantially increase the oxygen demand by increasing heart rate. Rather, increasing the oxygen demand could accelerate the ischemic damage.

In one embodiment, if the implantable pacing device 10 is a triple chamber ventricular pacemaker with leads in the right atrial appendage, the right ventricular apex, and the left ventricle, the pulse generator 26 can pace a lead (e.g., VDD-40) on the right or left ventricular wall with a short-sensed atrioventricular delay (e.g., about 30 milliseconds). The heart rate can be driven by the sinus rate so the oxygen demand does not substantially increase.

In some embodiments, unstable angina pectoris can be detected in any suitable manner in addition to acute myocardial infarction or alternatively from acute myocardial infarction. Angina pectoris is a term for chest pain or discomfort due to coronary heart disease. Typical angina is uncomfortable pressure, fullness, squeezing or pain in the center of the chest, responds well to nitrate drug therapy, and is reversible. The discomfort also may be felt in the neck, jaw, shoulder, back or arm. In some embodiments, the patient can use a control on the patient alerting device 34 to indicate he is experiencing symptoms and the patient alerting device 34 can communicate with the implantable pacing device 10 so that the pulse generator 26 begins providing asynchronous or dyssynchronous pacing to the patient.

The patients that can benefit from the cardiac conditioning system include, for example, those with already-implanted implantable pulse generators (e.g., single chamber, dual chamber, or triple chamber), and those patients at risk of myocardial infarction (e.g., patients having a history of myocardial infarction, coronary artery disease risk factors, diabetics, etc.).

The cardiac ischemic protection system can be a closed-loop therapy, and once activated, can significantly delay the progression of ischemia to necrosis, and therefore salvage myocardium and improve the prognosis of the patient (e.g., prevent heart failure). A particular advantage of such a system is to treat patients with asymptomatic ischemia, including silent ischemia and silent myocardial infarction.

The detector 22 can use any suitable type of detection method, algorithm, or technology. For example, suitable electrical technologies for the detection of acute myocardial infarction can include one or more of the following: ST segment deviation/digital sound processing (including heart rate); T-wave alternans; high frequency QRS; T-wave inversion; T-wave slew rate; intracardiac impedance; QT duration or QT dispersion; intrathoracic impedance; abrupt QRS morphology changes (excluding ectopic heartbeats having an origin elsewhere than in the sinoatrial node); ST segment maximum amplitude/changes; and abrupt heart rate changes. Suitable mechanical technologies for the detection of acute myocardial infarction can include one or more of the following: activity; contractility; heart sounds/digital sound processing; filling pressure (change in pressure over time—dP/dT); and wall motion. Suitable biochemical technologies for the detection of acute myocardial infarction can include one or more of the following: ischemia, myocardial infarction, inflammatory biomarkers, in particular lactate, and the enzymes LDH, creatine kinase (CK), and troponin; Atrial Natriuretic Peptide (ANP) or Brain Natriuretic Peptide (BNP); glucose sensor, oxygen partial pressure (pO2) sensor, or potassium ion (K+) sensor; clotting mechanism markers (e.g., thrombin, etc.); and endothelial activation sensors. A suitable thermal technology for the detection of acute myocardial infarction can include a temperature sensor. A suitable communication technology for the detection of acute myocardial infarction can include intrabody communication. Other suitable technologies for the detection of acute myocardial infarction can include one or more of the following: perfusion; vasodilatory responses; vagal activation; vasovagal tone; and autonomic reflex system changes. Moreover, any combination of chemical, electrical, and mechanical or other sensors could further increase the sensitivity and specificity of the diagnosis.

Also, in some embodiments, a pressure sensor can be used in further enhancing the diagnosis of ischemia. Also, in some embodiments, other biomedical sensors such as piezo-electrical sensors can be used to monitor and diagnose regional dysfunction associated with ischemia.

Figure 3:
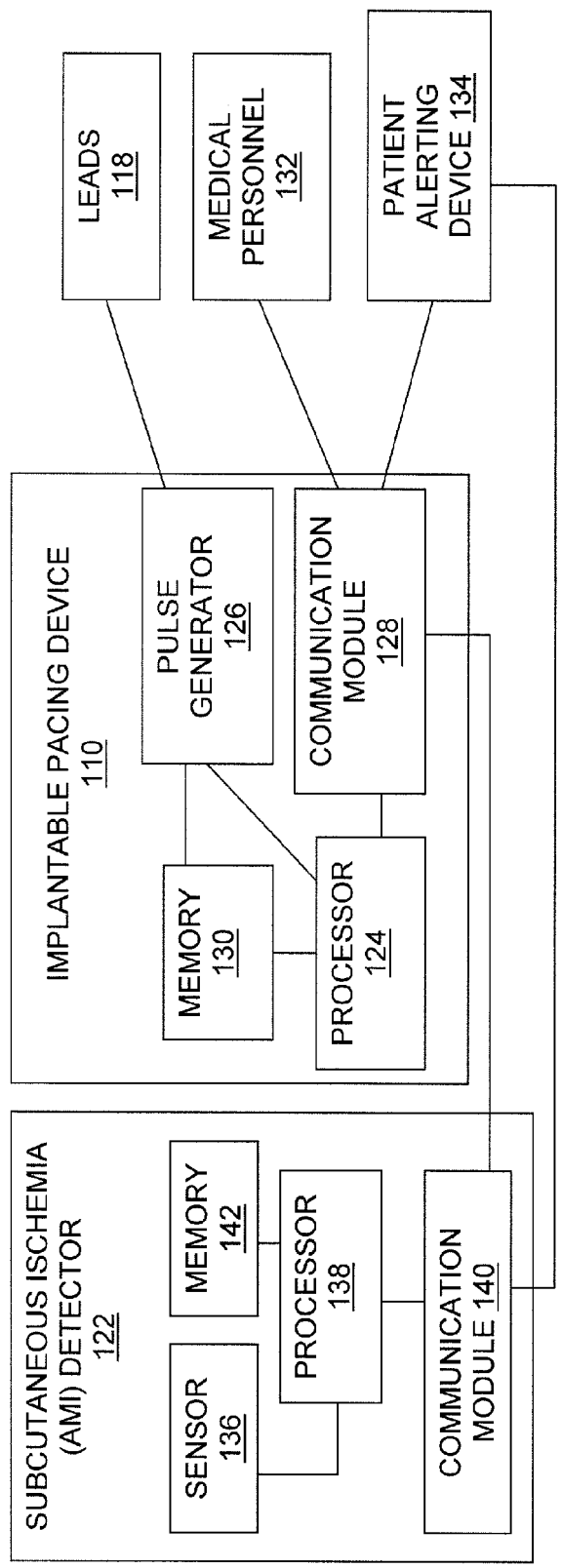
FIG. 3 is a block diagram illustrating a cardiac ischemic protection system including a subcutaneous diagnostic device in accordance with an embodiment of the present disclosure.

FIG. 3 illustrates a simplified block diagram of a cardiac ischemic protection system including an implantable pacing device 110 and a subcutaneous acute myocardial infarction detector 122. The implantable pacing device 110 can include a processor 124, a pulse generator 126, a communication module 128, and memory 130. The communication module 128 can communicate with medical personnel 132 and/or a patient alerting device 134. The subcutaneous acute myocardial infarction detector 122 can include one or more sensors 136, a processor 138, a communication module 140, and memory 142. In one embodiment, the subcutaneous acute myocardial infarction detector 122 can be a small diagnostic device (e.g., the size of a fingertip) that can be slipped under the patient's skin. The cardiac ischemic protection system of FIG. 3 can perform similar to the cardiac protection system of FIG. 2, except that the detection of the acute myocardial infarction is not performed by the implantable pacing device 10, but rather by a separate subcutaneous acute myocardial infarction detector 122. The communication module 140 of the subcutaneous acute myocardial infarction detector 122 can communicate with the communication module 128 of the implantable pacing device 110, which can then cause the pulse generator 126 to provide the asynchronous or dyssynchronous pacing via leads 18.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method of providing cardiac ischemic protection to a patient's heart, the method comprising:
   detecting at least one of acute myocardial infarction, angina pectoris, silent ischemia, and stunning;
   providing closed-loop dyssynchronous pacing to the patient's heart to at least one of precondition and postcondition the patient's heart in order to reduce ischemic damage,
   wherein the dyssynchronous pacing is configured to produce discordant motion of the ventricular walls of the patient's heart; and
   pacing the right ventricular apex with an atrioventricular delay with a dual chamber ventricular pacemaker,
   wherein the atrioventricular delay is about 30 milliseconds.

2. The method of claim 1 and further comprising alerting the patient to seek treatment after detecting at least one of acute myocardial infarction, angina pectoris, silent ischemia, and stunning.

3. The method of claim 1 and further comprising alerting medical personnel of the patient's condition after detecting at least one of acute myocardial infarction, angina pectoris, silent ischemia, and stunning.

4. The method of claim 1 and further comprising detecting acute myocardial infarction by detecting ST segment changes.

5. The method of claim 1 and further comprising providing pacing to precondition the patient's heart by providing one to ten periods of about five minutes of pacing and intermittent periods of sinus rhythm of about five minutes.

6. The method of claim 1 and further comprising providing continuous pacing to the patient's heart.

7. The method of claim 1 and further comprising manually activating the dyssynchronous pacing.

8. A cardiac ischemic protection system that conditions a patient's heart, the system comprising:
   a detector that detects at least one of acute myocardial infarction, angina pectoris, silent ischemia, and stunning; and
   a pulse generator that provides closed-loop dyssynchronous pacing to the patient's heart to at least one of precondition and postcondition the patient's heart in order to reduce ischemic damage,
   wherein the dyssynchronous pacing is configured to produce discordant motion of the ventricular walls of the patient's heart,
   wherein the pulse generator provides pacing to the right ventricular apex with an atrioventricular delay with a dual chamber ventricular pacemaker, and
   wherein the atrioventricular delay is about 30 milliseconds.

9. The system of claim 8 and further comprising an implantable pacing device that includes the detector.

10. The system of claim 8 and further comprising a patient alerting device that alerts the patient to seek treatment after the detector detects at least one of acute myocardial infarction, angina pectoris, silent ischemia, and stunning.

11. The system of claim 10 wherein the patient alerting device alerts medical personnel of the patient's condition after detecting at least one of acute myocardial infarction, angina pectoris, silent ischemia, and stunning.

12. The system of claim 8 wherein the detector detects acute myocardial infarction by detecting ST segment changes.

13. The system of claim 8 wherein the pulse generator provides pacing to precondition the patient's heart by providing one to ten periods of about five minutes of pacing and intermittent periods of sinus rhythm of about five minutes.

14. The system of claim 8 wherein the pulse generator provides pacing to precondition the patient's heart by providing continuous pacing.

15. The system of claim 8 wherein the dyssynchronous pacing is manually activated.

16. A method of providing cardiac ischemic protection to a patient's heart, the method comprising:
   detecting at least one of acute myocardial infarction, angina pectoris, silent ischemia, and stunning;
   providing closed-loop dyssynchronous pacing to the patient's heart to at least one of precondition and postcondition the patient's heart in order to reduce ischemic damage; and
   pacing one of the left ventricular wall and the right ventricular wall with an atrioventricular delay with a triple chamber ventricular pacemaker.

17. The method of claim 16 wherein the atrioventricular delay is about 30 milliseconds.

18. A method of providing cardiac ischemic protection to a patient's heart, the method comprising:
   detecting at least one of acute myocardial infarction, angina pectoris, silent ischemia, and stunning;
   providing closed-loop dyssynchronous pacing to the patient's heart to at least one of precondition and postcondition the patient's heart in order to reduce ischemic damage; and
   driving the patient's heart rate at sinus rate so that oxygen demand does not substantially increase.

19. A cardiac ischemic protection system that conditions a patient's heart, the system comprising:
   a detector that detects at least one of acute myocardial infarction, angina pectoris, silent ischemia, and stunning; and
   a pulse generator that provides closed-loop dyssynchronous pacing to the patient's heart to at least one of precondition and postcondition the patient's heart in order to reduce ischemic damage;
   wherein the pulse generator provides pacing to one of the left ventricular wall and the right ventricular wall with an atrioventricular delay with a triple chamber ventricular pacemaker.

20. The system of claim 19 wherein the atrioventricular delay is about 30 milliseconds.

21. A cardiac ischemic protection system that conditions a patient's heart, the system comprising:
- a detector that detects at least one of acute myocardial infarction, angina pectoris, silent ischemia, and stunning; and
- a pulse generator that provides closed-loop dyssynchronous pacing to the patient's heart to at least one of precondition and postcondition the patient's heart in order to reduce ischemic damage;

wherein the patient's heart rate is driven at sinus rate so that oxygen demand does not substantially increase.

* * * * *